US009135397B2

(12) United States Patent
Denyer et al.

(10) Patent No.: US 9,135,397 B2
(45) Date of Patent: Sep. 15, 2015

(54) SYSTEM AND METHOD FOR ENABLING THERAPEUTIC DELIVERY OF AEROSOLIZED MEDICAMENT TO A PLURALITY OF SUBJECTS TO BE MONITORED

(75) Inventors: Jonathan S. H. Denyer, Chichester (GB); Michael James Robbert Leppard, Hunston (GB); Ian Philip Rabbetts, Hayling Island (GB); Anthony Dyche, Hayling Island (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 481 days.

(21) Appl. No.: 13/384,791

(22) PCT Filed: Jul. 12, 2010

(86) PCT No.: PCT/IB2010/053185
§ 371 (c)(1),
(2), (4) Date: Jan. 19, 2012

(87) PCT Pub. No.: WO2011/021117
PCT Pub. Date: Feb. 24, 2011

(65) Prior Publication Data
US 2012/0304987 A1 Dec. 6, 2012

Related U.S. Application Data

(60) Provisional application No. 61/234,265, filed on Aug. 15, 2009.

(51) Int. Cl.
*A61M 16/10* (2006.01)
*G06F 19/00* (2011.01)

(52) U.S. Cl.
CPC .................................. *G06F 19/3418* (2013.01)

(58) Field of Classification Search
CPC ............ A61M 15/00; A61M 15/0045; A61M 11/005; A61M 15/0085; A61M 16/10; A61M 16/14; A61M 16/0051; A61M 16/00; A61M 11/06; A61M 15/009; A61M 2015/0003; A61M 2205/52; A61M 2015/0043; A61M 2015/0055; A61M 2205/6018; A61M 2205/8206; A61M 15/0028; A61M 15/0065; A61M 15/0086; A61M 2015/0048; A61M 2015/005; A61M 2015/0096; A61M 2016/0021; A61M 2202/064; A61M 2205/3546; A61M 2205/3569; A61M 2205/3576; A61M 2205/3592; A61M 2205/505; A61M 2205/581; A61M 2205/80; A61M 2206/16; A61M 11/041; A61M 15/08; A61M 16/0057; A61M 16/0066; A61M 16/06; A61M 2011/047; A61M 2015/001; A61M 2015/008; A61M 2016/0027; A61M 2016/0039; A61M 2016/109; A61M 2016/161; A61M 2205/3561; A61M 2205/50; A61M 2205/6054; A61M 2205/6072; A61M 2206/14; A61M 2230/06; A61M 2230/201; A61M 2230/205; A61M 2230/30; A61M 31/002; A61M 5/14276; G06F 19/3462; G06F 19/3418; G07F 17/0092; A61B 5/087; A61B 5/4839; A61B 5/08
USPC ............. 128/200.24, 200.11–203.23, 203.12, 128/203.15
See application file for complete search history.

(56) References Cited

U.S. PATENT DOCUMENTS

| | | | |
|---|---|---|---|
| 6,584,971 B1 | 7/2003 | Denyer et al. | |
| 6,648,820 B1 | 11/2003 | Sarel | |
| 6,863,224 B2 | 3/2005 | Terada et al. | |
| 8,261,738 B2 * | 9/2012 | Denyer et al. | 128/203.14 |
| 8,607,786 B2 | 12/2013 | Denyer | |
| 2003/0098022 A1 | 5/2003 | Nakao et al. | |
| 2004/0158349 A1 | 8/2004 | Bonney et al. | |
| 2005/0172958 A1 | 8/2005 | Singer et al. | |
| 2006/0243277 A1 | 11/2006 | Denyer et al. | |
| 2008/0004540 A1 | 1/2008 | Nakao et al. | |
| 2008/0047553 A1 | 2/2008 | Denyer et al. | |
| 2009/0025718 A1 | 1/2009 | Denyer et al. | |

FOREIGN PATENT DOCUMENTS

| | | |
|---|---|---|
| EP | 1525893 A2 | 4/2005 |
| JP | 2003159332 A | 6/2003 |
| WO | 9312823 A2 | 8/1993 |
| WO | 0130231 A2 | 5/2001 |
| WO | 2006048417 A1 | 5/2006 |

OTHER PUBLICATIONS

Mc Namara et al, "Open Adherence Monitoring Using Routine Data Download from an Adaptive Aerosol Delivery Nebuliser in Children with Cystic Fibrosis", Journal of Cystic Fibrosis, 2009, pp. 1-6.
"Clinician's Training Manual", Respironics I-NEB™ AAD® System, Undated.

* cited by examiner

*Primary Examiner* — Annette Dixon
(74) *Attorney, Agent, or Firm* — Michael W. Haas

(57) ABSTRACT

A server is configured to be communicatively linked with drug delivery devices used by a plurality of different subjects to receive aerosolized medicament as part of a therapy regime. The server provides a user with a user interface that enables the user to access therapy information related to the therapy of a plurality of different subjects. This may facilitate the monitoring of therapy received by the plurality of subjects.

15 Claims, 9 Drawing Sheets

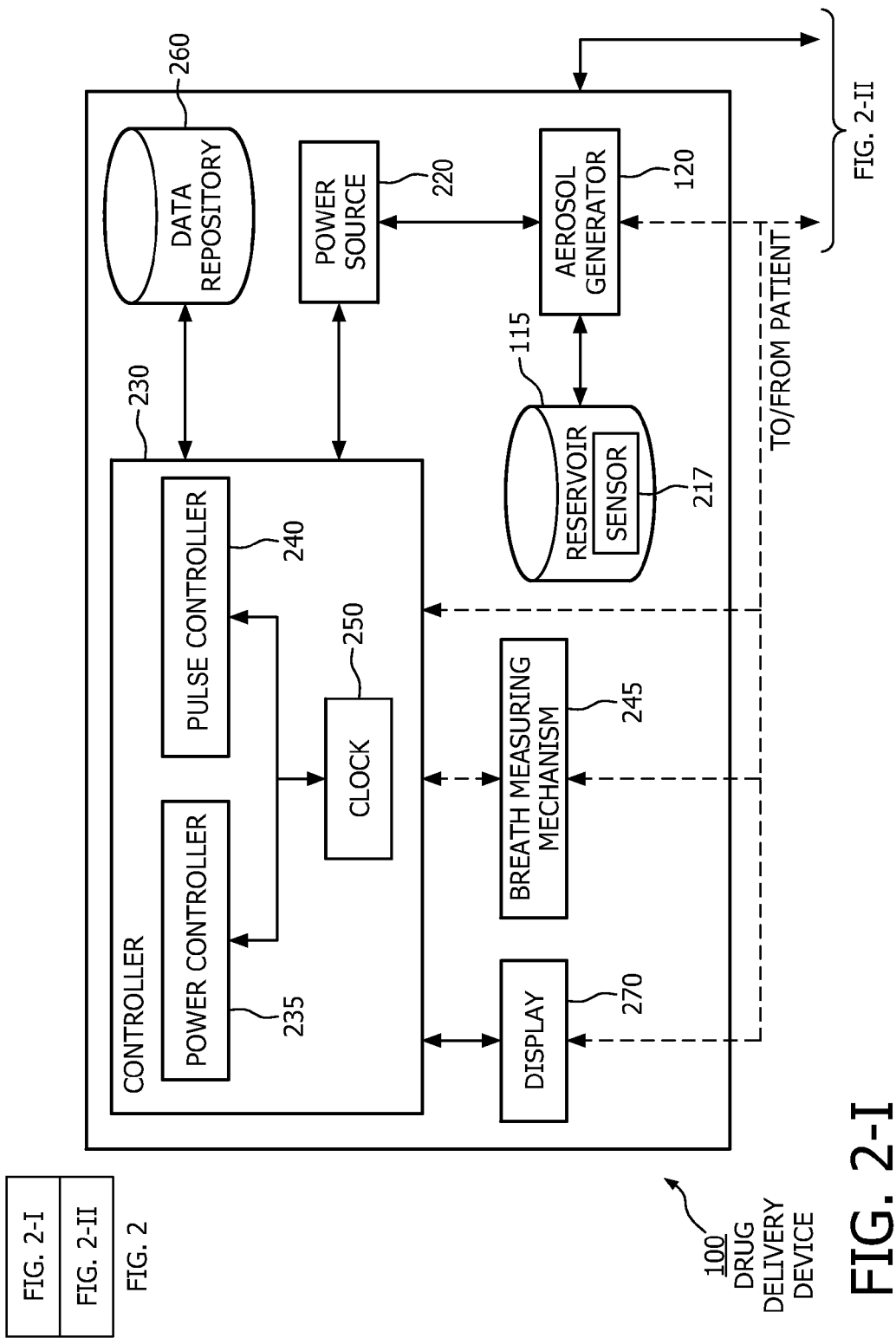

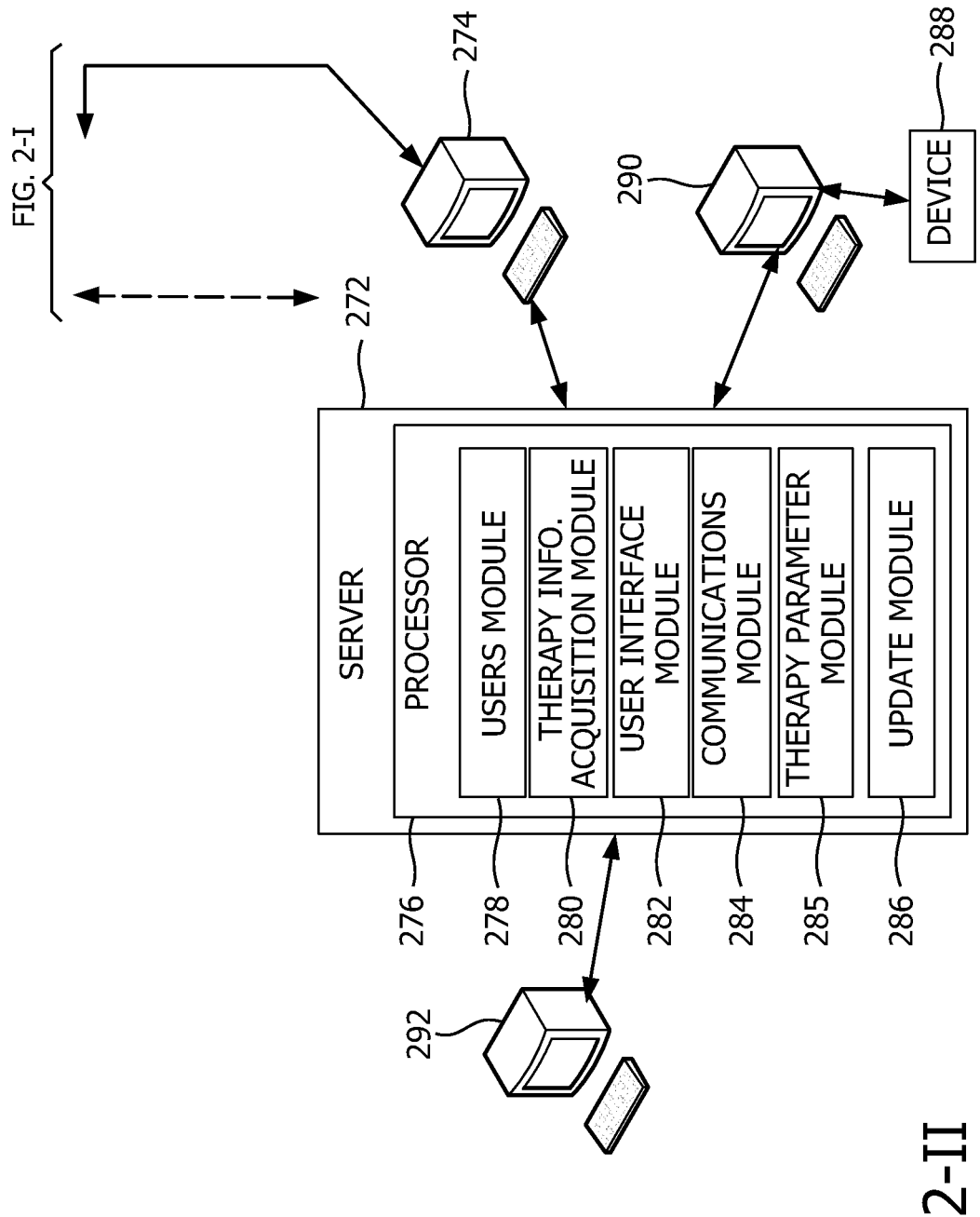
FIG. 2-II

US 9,135,397 B2

SYSTEM AND METHOD FOR ENABLING THERAPEUTIC DELIVERY OF AEROSOLIZED MEDICAMENT TO A PLURALITY OF SUBJECTS TO BE MONITORED

CROSS-REFERENCE TO RELATED APPLICATIONS

This application is related to U.S. patent application Ser. No. 12/175,486, filed on Jul. 18, 2008, now U.S. Pat. No. 8,261,738, granted on Sep. 11, 2012, which is incorporated herein in its entirety.

BACKGROUND OF THE PRESENT APPLICATION

Field of the Present Application

The invention relates to providing centralized, network-based access to therapy information relating to and control over therapy regimes administered to a plurality of subjects, wherein the therapy regimes include the administration of aerosolized medicament via drug delivery devices.

Aerosol drug delivery devices are often used in medical treatment to provide drugs in a form that can be inhaled by a patient. Drugs in powder, liquid, or other forms may be aerosolized using various techniques (e.g., using a piezoelectric member) to enable the drug to be absorbed through the patient's air passage. As such, aerosol drug treatments may be administered for respiratory ailments (e.g., asthma) or other treatments where a patient inspires drugs while breathing.

Aerosol drug treatments are typically designed to administer a specific dosage of drug over a given period of time. Maintaining uniformity in treatment (i.e., dosage and treatment time) can often be a factor in the effectiveness of the treatment or the marketability of a treatment system, among other things. Existing systems and techniques for administering aerosol drug treatments, however, often fail to adequately account for various factors that may interfere with uniformity in treatment. For example, an administered drug dosage or treatment duration may be non-uniform due to variations in a breathing pattern of a patient, properties of a drug delivery device (e.g., output rate), or other factors.

Existing systems suffer from these and other problems.

SUMMARY OF THE PRESENT APPLICATION

One aspect of the invention relates to a system configured to enable one or more users to monitor therapy of a plurality of subjects, wherein such therapy includes the delivery of aerosolized medicament. In one embodiment, the system comprises a server comprising one or more processors configured to execute one or more computer program modules, the one or more modules comprising a therapy information acquisition module, a user interface module, and a communications module. The therapy information acquisition module is configured to obtain, over a communications network, therapy information from a plurality of drug delivery apparatuses, wherein the plurality of drug delivery apparatuses comprise at least a first drug delivery apparatus associated with a first subject and a second drug delivery apparatus associated with a second subject, wherein each of the first drug delivery apparatus and the second drug delivery apparatus include a mesh used in the aerosolization of medicament, and wherein the therapy information obtained comprises (i) information related to the breathing patterns of the first subject and the second subject during usage of the first drug delivery apparatus and the second drug delivery apparatus, respectively, and/or (ii) information related to a condition of the mesh included in the first drug delivery device and a condition of the mesh included in the second drug delivery device. The user interface module is configured to generate a definition of a user interface for a user that enables the user to selectively view therapy information obtained by the therapy information acquisition module from the first drug delivery apparatus and the second drug delivery apparatus. The communications module is configured to provide, over a communications network, the definition of the user interface to a client computing platform associated with the user.

Another aspect of the invention relates to a computer implemented method of enabling one or more users to monitor therapy of a plurality of subjects remotely, wherein such therapy includes the delivery of aerosolized medicament, and wherein the method is implemented by a server comprising one or more processors configured to execute one or more computer program modules. In one embodiment, the method comprises executing one or more computer program modules on the one or more processors of the server to obtain, over a communications network, therapy information from a plurality of drug delivery apparatuses, wherein the plurality of drug delivery apparatuses comprise at least a first drug delivery apparatus associated with a first subject and a second drug delivery apparatus associated with a second subject, wherein each of the first drug delivery apparatus and the second drug delivery apparatus include a mesh used in the aerosolization of medicament, and wherein the therapy information obtained comprises (i) information related to the breathing patterns of the first subject and the second subject during usage of the first drug delivery apparatus and the second drug delivery apparatus, respectively, and/or (ii) information related to a condition of the mesh included in the first drug delivery device and a condition of the mesh included in the second drug delivery device; executing one or more computer program modules on the one or more processors of the server to generate a definition of a user interface for a user that enables the user to selectively view therapy information obtained by the therapy information acquisition module from the first drug delivery apparatus and the second drug delivery apparatus; and executing one or more computer program modules on the one or more processors of the server to provide, over a communications network, the definition of the user interface to a client computing platform associated with the user so that the client computing platform presents the user interface to the user.

Another aspect of the invention relates to a system configured to enable one or more users to monitor therapy of a plurality of subjects remotely, wherein such therapy includes the delivery of aerosolized medicament. In one embodiment, the system comprises means for obtaining, over a communications network, therapy information from a plurality of drug delivery apparatuses, wherein the plurality of drug delivery apparatuses comprise a first drug delivery apparatus associated with at least a first subject and a second drug delivery apparatus associated with a second subject, wherein each of the first drug delivery apparatus and the second drug delivery apparatus include a mesh used in the aerosolization of medicament, and wherein the therapy information obtained comprises (i) information related to the breathing patterns of the first subject and the second subject during usage of the first drug delivery apparatus and the second drug delivery apparatus, respectively, and/or (ii) information related to a condition of the mesh included in the first drug delivery device and a condition of the mesh included in the second drug delivery device; means for generating a definition of a user interface for a user that enables the user to selectively view therapy information obtained by the therapy information acquisition module from the first drug delivery apparatus and the second drug delivery apparatus; and means for providing, over a communications network, the definition of the user interface to a client computing platform associated with the user so that the client computing platform presents the user interface to the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 2-I and 2-II illustrate an exemplary system for maintaining consistency for aerosol drug delivery treatments of a plurality of subjects according to various aspects of the invention.

DETAILED DESCRIPTION OF THE PRESENT APPLICATION

Figure 1:
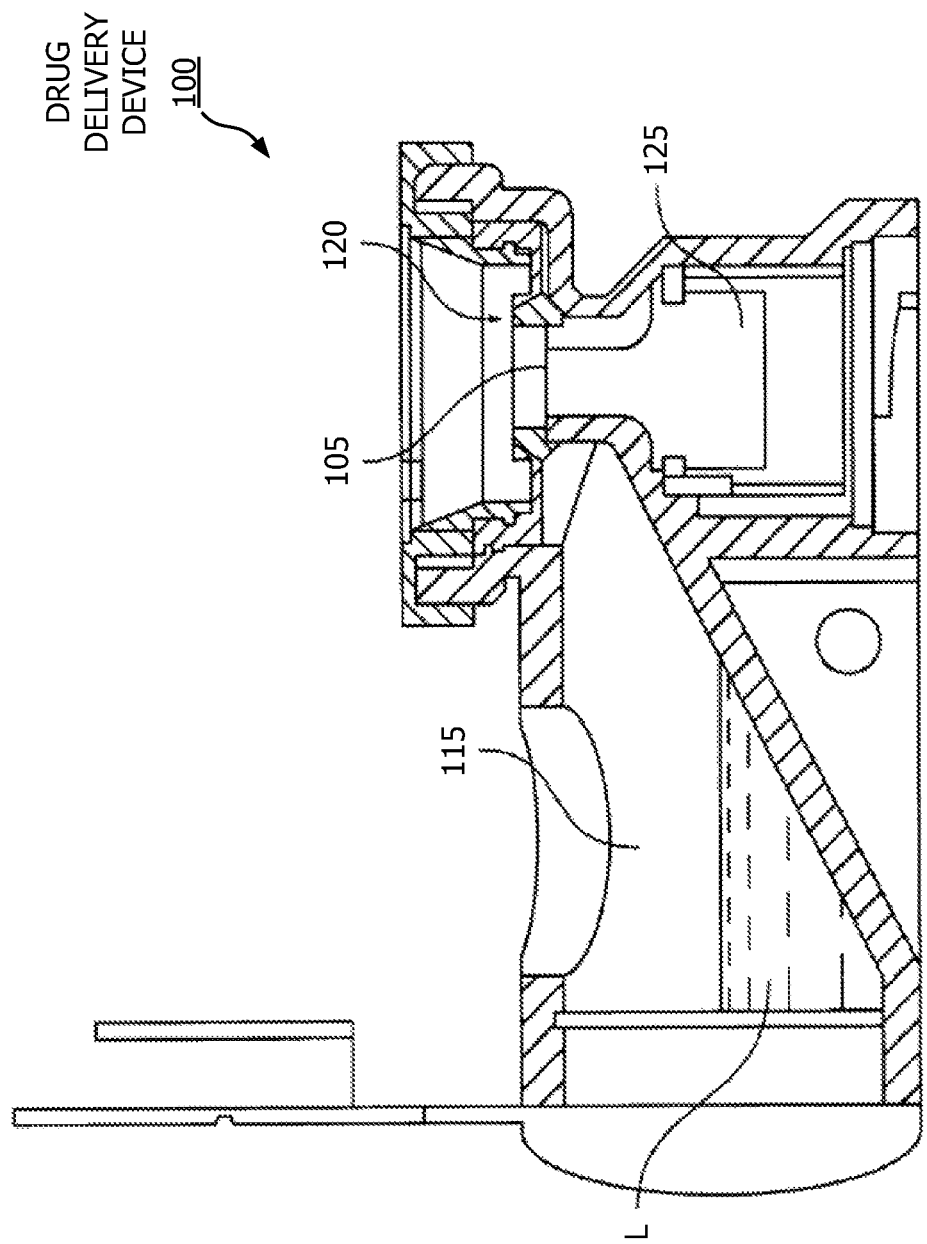
FIG. 1 illustrates an exemplary aerosol drug delivery device according to various aspects of the invention.

According to various aspects of the invention, as illustrated in FIG. 1, for example, an aerosol drug delivery device 100 may be used to administer an aerosol form of a liquid drug L for inspiration by a patient. For example, device 100 may include a reservoir 115 for containing a liquid drug L and an aerosol generator 120.

The aerosol generator 120, in one embodiment, may take the form of a mesh member 105 in combination with a horn oscillating member 125 for nebulizing or otherwise aerosolizing the liquid drug L. However, as discussed in more detail later, this type of aerosol generator 120 is a non-limiting example of the many different types of aerosol generators that can be used within the scope of the present invention. The mesh member 105 is, in one embodiment, may be mounted to an end surface of a distal end of the horn oscillating member 125. The drug delivery device 100 may incorporate any suitable power source (as will be discussed later) to electrically drive the horn oscillating member 125. As such, the horn oscillating member 125 may force the liquid L through a plurality of fine apertures or pores in mesh member 105, thereby producing an aerosolized form of liquid drug L that can be inspired by a patient.

The reservoir 115 can be any chamber, container, or canister that may contain a dosage of liquid drug. In various implementations, aerosol generator 120 and reservoir 115 device 100 may be constructed and arranged as described in U.S. Pat. No. 6,863,224 ("the '224 patent"), issued Mar. 8, 2005, entitled "Liquid Spray Device," the disclosure of which is hereby incorporated by reference in its entirety. It should be emphasized, however, that the '224 patent discloses but one example of the type of aerosol generator and reservoir that can be employed with the teachings of the present invention, as will be apparent from the farther descriptions herein.

FIGS. 2-I and 2-II are schematic diagrams representing various components of the exemplary drug delivery device 100 of FIG. 1, and which may be configured to maintain consistent treatment times for aerosol drug delivery treatments in accordance with various aspects of the invention. In one embodiment, the reservoir 115 cooperates with or includes a sensor 217 that can be used to determine whether the liquid drug L in the reservoir 115 has been fully depleted, as will be described in more detail later.

The aerosol generator 120 may be in electrical communication with power source 220, which drives the operation (e.g., nebulizing action) of the aerosol generator 120. For example, in the embodiment where the aerosol generator 120 comprises mesh 105 and horn oscillating member 125, the power source 220 drives the operation (e.g., on/off) of the horn oscillating member 125 and the power level applied to the horn oscillating member 125.

Drug delivery device 100 may administer the drug dosage in reservoir 115 by aerosolizing the drug dosage contained therein over successive aerosol pulses for inspiration by a patient (e.g., one pulse per patient inhalation). For example, power source 220 may deliver successive pulses of power to aerosol generator 120, causing the horn oscillating member 125 to produce corresponding pulses of aerosolized drug (e.g., liquid droplets or vapor). Pulses of power (and corresponding pulses of aerosolized drug) may continue to be delivered until all liquid (i.e., the entire dose) in reservoir 115 has been aerosolized (and ideally inhaled by the patient), thereby completing the administered treatment.

As noted above, aerosol generator 120 may produce the aerosolized form of the liquid drug L using any type of nebulizer or aerosol generating mechanism that can turn the liquid drug L into aerosol and/or droplets that can be inhaled by the patient. For example, as illustrated in FIG. 1, liquid drug L disposed in reservoir 115 may reach a proximal point of contact between a distal end of oscillating horn member 125 and mesh 105 (e.g., a metallic or non-metallic screen having a plurality of fine apertures). Referring back to FIGS. 2-I and 2-II, the power source 220 may deliver a pulse of power to aerosol generator 120, causing the horn 125 to vibrate and drive the liquid drug through the mesh 105, detaching the liquid into an aerosolized form. It will be apparent, however, that various other aerosol generators 120 may be used, including jet nebulizers, vibrating meshes, vibrating horns, nozzles that use Raleigh breakup theory, piezoelectric crystal technology, or other nebulizing devices or techniques known in the art. It should be appreciated that these are non-limiting examples of the type of aerosol generators that can be used with the present invention, and that any suitable device that can nebulize or aerosolize a liquid drug for this application can be used.

As can be appreciated from the discussion above, aerosol generator 120 may be configured to receive pulses of power from power source 220 until all of the liquid in the chamber 115 has been aerosolized for inspiration by the patient. As such, a uniform drug dosage may be administered in every treatment instance. For various reasons, however, aerosol generator 120, in itself may not necessarily maintain a uniform duration of treatment for every treatment. For example, a breathing pattern of a patient (e.g., an inhalation to exhalation ratio, a breathing frequency, etc.) may impact a rate of drug administration, potentially impacting treatment time. In another example, the mesh 105 of aerosol generator 120 may become dirty over a course of treatment, or a reusable mesh may become dirtier over a course of successive treatments, or meshes may be interchanged between treatments, or the mesh may degrade over time, all of which may be among contributing factors potentially impacting treatment time (e.g., by reducing a rate at which generator 120 outputs the aerosolized drug).

Accordingly, as shown in FIGS. 2-I and 2-II, a controller 230 is coupled to power source 220 to minimize variations in treatment time. Controller 230 may be a hardware controller (e.g., an electrical circuit or microprocessor), a software controller (e.g., computer-executable instructions), or any suitable combination thereof. Controller 230 may vary a level of power delivered to aerosol generator 120 by the power source 220 based on various factors, including a breathing pattern of a patient, a cleanliness or dirtiness of a mesh, or variations in an output rate of generator 120, among other things.

Controller 230 may include a clock 250 for tracking an elapsed duration of a treatment, a power controller 235, and a pulse controller 240 (e.g., combinations of hardware components and computer-executable instructions) for electronically controlling power levels and pulse lengths applied by the power source 220 to the aerosol generator 120. It should be appreciated that the controller 230 can be considered a single device incorporating the functionalities of each of clock 250, power controller 235, and pulse controller 240. Alternatively, each of the elements 250, 235, and 240 may be considered to be separate components or modules that may be provided separately, or outside of controller 230.

The drug delivery device 100 may also include a breath measuring mechanism 245, operatively connected with controller 230, and which is operable to monitor or otherwise measure a patient's breathing pattern. The breathing pattern may include measurements of one or more of the patient's tidal volume, flow rate, inhalation rate, exhalation rate, a ratio of inhalation to exhalation rates, or other characteristics of a patient's breathing. In various implementations, the breath measuring mechanism 245 can include a pressure sensor for detecting the pressure within an atomizing section of a nebulizer, a respiratory valve, a patient port, or other suitable structure for measuring the patient's breathing pattern. As such, in various embodiments, the patient's breathing pattern (e.g., inhalation duration) could be measured by triggering a timer based on the pressure detected by the sensor and measuring the duration of inspiration. As another example, the breath measuring mechanism can employ a sensor that measures gas concentration or light dispersion, to measure a concentration of aerosolized medication in a mouthpiece (or elsewhere), in conjunction with a flow sensor, in order to estimate an amount of medication inhaled per breath. In one embodiment, the breathing pattern may be measured using techniques and structures described in U.S. Pat. No. 6,584,971 ("the '971 patent"), issued Jul. 1, 2003, entitled "Drug Delivery Apparatus," the disclosure of which is hereby incorporated by reference in its entirety. It will be appreciated, however, that the '971 patent illustrates but one example of a way in which to measure a patient's breathing pattern, and that other structures or techniques can be used.

Controller 230 may be coupled to a data repository 260 (e.g., a built-in memory, a removable media or memory, etc.). The data repository 260 may be capable of storing settings that describe the treatment to be administered and a log of administered therapy information to assist in performing diagnostics or maintenance. Any of the settings may be manually input to data repository 260 through an input interface, or may be pre-coded into the data repository 260. The settings in data repository 260 may include information relating to nominal treatment duration, liquid drug dosage, and/or power levels, among other information for maintaining consistency for an aerosol drug delivery treatment. For instance, the settings may relate to a nominal output rate for the mesh (e.g., expressed in milliliters per minute), which may be defined as a function of one or more of the mesh grading, a nominal power setting, a medication chamber dosage (or chamber volume) (e.g., milliliters), and a target treatment duration, or any combination thereof. Further, the settings may include additional information used to vary a power level delivered to aerosol generator 120, including a current power setting, a maximum power setting, a minimum power setting, threshold inhalation to exhalation ratios, and deltas for increasing or decreasing power, among other things.

Clock 250 may begin when a treatment starts, thereby actively measuring an elapsed time of the treatment. Each time that the patient breathes during the treatment, breath measuring mechanism 245 may measure one or more of the patient's inhalation duration, exhalation duration, a ratio of the inhalation to exhalation durations, tidal volume, flow rate, any combination of the foregoing, or other respiration characteristics to determine the patient's current breathing pattern (e.g., as described in the incorporated '971 patent). Based on these measurements, pulse controller 240 may determine an optimal length of a pulse delivered by power source 220 to aerosol generator 120. The optimal duration for a pulse may last from when an inhalation begins (or shortly thereafter) until a point in the inhalation when the remaining volume to be inspired equals the estimated end volume (e.g., the volume of the patient's upper airway). The pulse would then cease, allowing the remaining volume to be cleared from aerosol generator 120 and inspired into the patient's lungs. For example, in various other implementations, the length of a pulse may be determined as described in the '971 patent (i.e., Pulse time=(average inhalation time).times.(average tidal volume-end volume)/(average tidal volume)). It will be appreciated, however, that the '971 patent provides but one example of a technique for determining pulse length, and that other methods may be used without departing from the scope and spirit of the invention. For example, various implementations may control the pulse length as described in co-pending U.S. patent application Ser. No. 10/535,867, entitled "Inhalation Method and Apparatus," filed Nov. 20, 2003, now U.S. Pat. No. 8,607,786, granted on Dec. 17, 2013, the disclosure of which is hereby incorporated by reference in its entirety. In such implementations, the pulse length may be controlled to end a predetermined amount of time prior to when the patient is expected to stop inhaling, such that a period of time remains at the end of the breath to allow for sedimentation of the aerosol.

Upon measuring the patient's breathing pattern (e.g., inhalation duration, exhalation duration, ratio of the inhalation to exhalation durations, tidal volume, end volume, etc.), the pattern may be provided to power controller 235 for determining whether to vary a power level for the pulse delivered in a subsequent breath (e.g., based a relationship between the breathing pattern and threshold inhalation to exhalation ratios, as will be described herein). Further still, power controller 235 may use the measured elapsed treatment time 415, as measured by clock 250, to determine whether to increase the power level for the subsequent pulse. As such, various techniques may be used by power controller 235 to control a time for a treatment by determining whether to increase and/or decrease the power level during the treatment (e.g., to maintain consistent treatment times, reduce treatment times, increase treatments, achieve a target treatment time, or otherwise), as described in greater detail in FIGS. 3-4 below.

As is shown in FIGS. 2-I and 2-II, drug delivery device 100 is in communication with a server 272. This communication is achieved over a communications network. The communications network may include the Internet, or a more localized network, such as an intranet associated with a clinic (or set of clinics), a hospital (or set of hospitals), or other entities.

In one embodiment, communication between drug delivery device 100 and server 272 takes place indirectly through a client computing platform 274 associated with the user of drug delivery device 100. The client computing platform 274 may include one or more of a laptop computer, a desktop computer, a netbook, a smartphone, and/or other client computing platforms. The client computing platform 274 is, at least intermittently, communicatively coupled with drug delivery device 100 to obtain information therefrom and/or provide instructions or other communications thereto. This communication may be accomplished, for example, via a wireless connection (e.g. Bluetooth, WiFi, infrared, WiMax, and/or other wireless connection), and/or wired connection.

The client computing platform 274 may include one or more processors configured to execute one or more computer programming modules. At least some of the one or more computer programming modules executed on the one or more processors of client computing platform 274 include software modules associated with a software application that provides the functionality attributed herein to client computing platform 274. These software modules are stored on electronic storage media that is accessible to the one or more processors of client computing platform 274.

The information received on client computing platform 274 from drug delivery device 100 may include, for instance, downloads of therapy information from data repository 260 to client computing platform 274. As will be discussed further below, the therapy information may include, for example, one or more of a total aerosol (e.g., a horn) actuation time, a total amount of time the patient spent inhaling, a total amount of time the patient spent exhaling, information related to the power level at which drug delivery device 100 was operated during therapy, and/or other therapy information. Based on this information, client computing platform 274 may provide a user interface to the patient (and/or caregiver or other user) a user interface that enables the patient to access indications of the effectiveness of the therapy, the compliance of the patient with a prescribed therapy regime, the operational efficiency of drug delivery device 100, and/or other information related to the therapy, and/or other information related to the therapy.

As was stated above, client computing platform 274 is communicatively coupled with server 272 via a network. As is shown in FIG. 1, server 272 includes a processor 276. Processor 276 is configured to provide information processing capabilities in server 272. As such, processor 276 may include one or more of a digital processor, an analog processor, a digital circuit designed to process information, an analog circuit designed to process information, a state machine, and/or other mechanisms for electronically processing information. Although processor 276 is shown in FIGS. 2-I and 2-II as a single entity, this is for illustrative purposes only. In some implementations, processor 276 may include a plurality of processing units. These processing units may be physically located within the same device, or processor 276 may represent processing functionality of a plurality of devices (e.g., a plurality of servers) operating in coordination to provide the functionality attributed herein to server 272.

As is shown in FIGS. 2-I and 2-II, processor 276 is configured to execute one or more computer program modules. The one or more computer program modules may include one or more of a users module 278, a therapy information acquisition module 280, a user interface module 282, a communications module 284, a therapy parameter module 285, an update module 286, and/or other modules. Processor 276 may be configured to execute modules 278, 280, 282, 284, 285, and/or 286 by software; hardware; firmware; some combination of software, hardware, and/or firmware; and/or other mechanisms for configuring processing capabilities on processor 276.

It should be appreciated that although modules 278, 280, 282, 284, 285, and 286 are illustrated in FIGS. 2-I and 2-II as being co-located within a single processing unit, in implementations in which processor 276 includes multiple processing units, one or more of modules 278, 280, 282, 284, 285 and/or 286 may be located remotely from the other modules. The description of the functionality provided by the different modules 278, 280, 282, 284, 285, and/or 286 set forth below is for illustrative purposes, and is not intended to be limiting, as any of modules 278, 280, 282, 284, 285, and/or 286 may provide more or less functionality than is described. For example, one or more of modules 278, 280, 282, 284, 285, and/or 286 may be eliminated, and some or all of its functionality may be provided by other ones of modules 278, 280, 282, 284, 285, and/or 286. As another example, processor 276 may be configured to execute one or more additional modules that may perform some or all of the functionality attributed below to one of modules 278, 280, 282, 284, 285, and/or 286.

The users module 278 is configured to manage one or more user profiles of users that are provided with access to therapy information obtained by server 272 from drug delivery device 100. As used herein the term "user" may include a caregiver, a researcher, an administrator, and/or other individuals that should be provided with access to therapy information associated with the patient using drug delivery device 100. The user profiles may include one or more of authentication information that enables the user to be authenticated to server 272 and/or associated with a particular user profile, configuration preferences associated with the users, and/or other information associated with the individual users.

It will be appreciated that drug delivery device 100 is not the only drug delivery device for which server 272 receives therapy information. For example, in FIGS. 2-I and 2-II, a second drug delivery device 288 used by a patient that is different than the patient using drug delivery device 100 is also communicatively linked with server 272 (e.g., via a client computing platform 290). In one embodiment, the information related to individual users included in the user profiles managed by users module 278 includes access privileges that indicate which drug delivery devices the individual users should be given access to. The access privileges may even indicate specific types of therapy information for which access should be given to a given user (e.g., information related to performance efficiency or effectiveness of a device, but not information related to patient respiration, treatment, and/or compliance).

The therapy information acquisition module 280 is configured to obtain therapy information from a plurality of drug delivery devices, including drug delivery devices 100 and 288. In one embodiment, this includes communicating with client computing platforms 274 and 290 to receive therapy information that has been transferred from drug delivery devices 100 and 288 to client computing platforms 274 and 290, respectively.

The user interface module 282 is configured to generate a definition of a user interface that defines a user interface for a user enabling the user to selectively view therapy information obtained by therapy information acquisition module 280. This includes enabling a user to select a specific patient or set of patients, and to view therapy information associated with the specific patient or set of patients based on the selection. The user interface defined by user interface module 282 further enables a user to select a therapy information type and/or analysis based on the therapy information, and to view the selected information type and/or analysis.

In one embodiment, the definition of the user interface generated by user interface module 282 includes a definition of a web page that can be viewed in a Web browser on a client computing platform. The definition of the web page may include, for example, HTML, dHTML, XML, JAVA, Flash, and/or information encoded in other formats that are readable by a Web browser. In one embodiment, the definition of the user interface generated by user interface module 282 is generated for a more specialized client side application. For example, the client side application may already include views for selectively viewing therapy information, and the definition of the user interface generated by user interface module 282 may include merely values for the therapy information that is viewable within a given view provided by the client side application. In this embodiment, the client side application receives the values for the therapy information included in the definition of the user interface that inserts some or all of the values (as appropriate) into the corresponding portions of a view.

Figure 6:
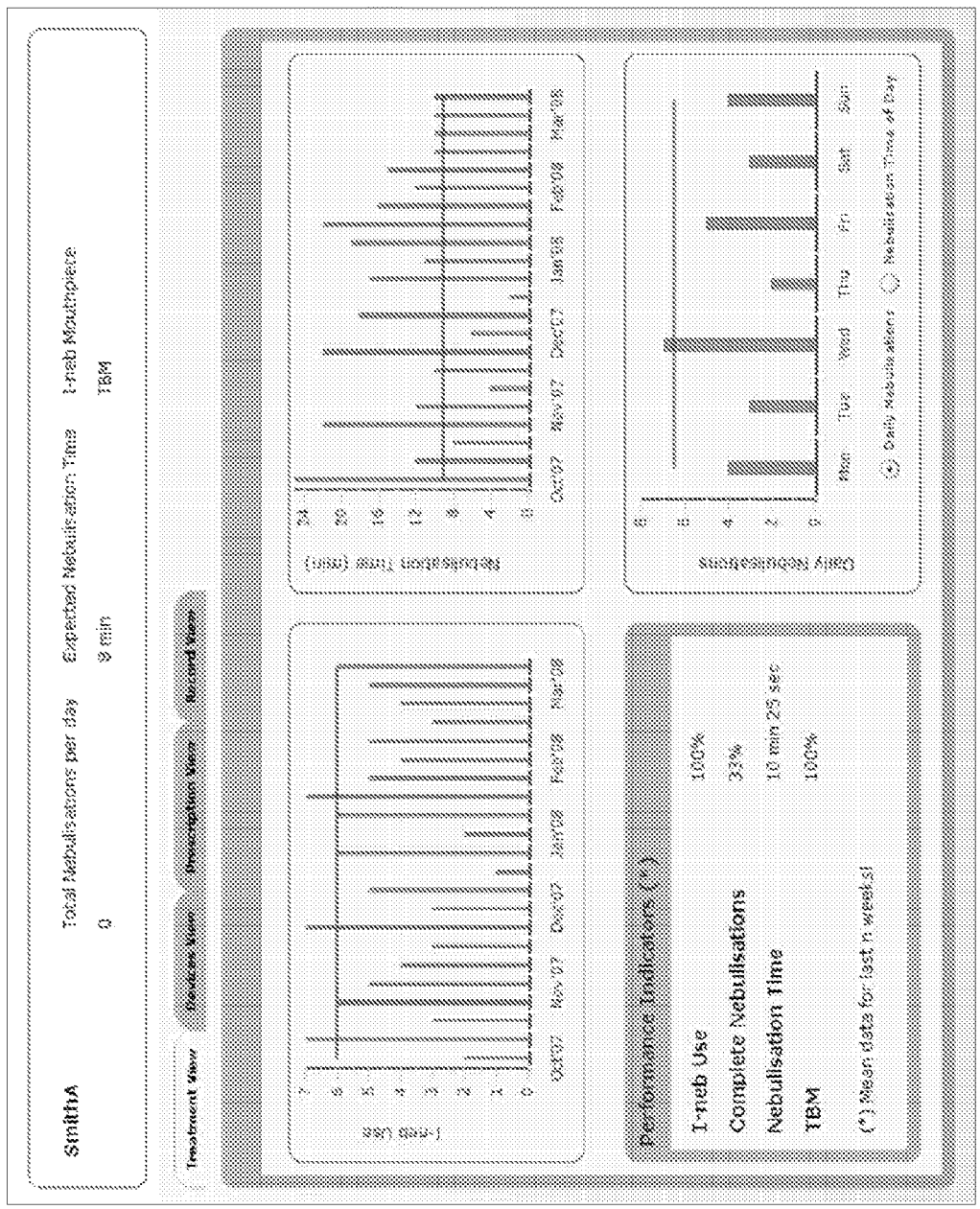
FIG. 6 illustrates a treatment view of a user interface that provides information to a user about the therapy received by a subject according to various aspects of the invention.

By way of illustration, FIG. 6 shows a view of the user interface defined by user interface module 282 that includes therapy information related to patient compliance to a treatment regime. This view may be referred to as a "treatment view." As can be seen in FIG. 6, the treatment view provides the user with information about the frequency and/or duration of treatments received by a patient or group of patients, and/or other information.

Figure 7:
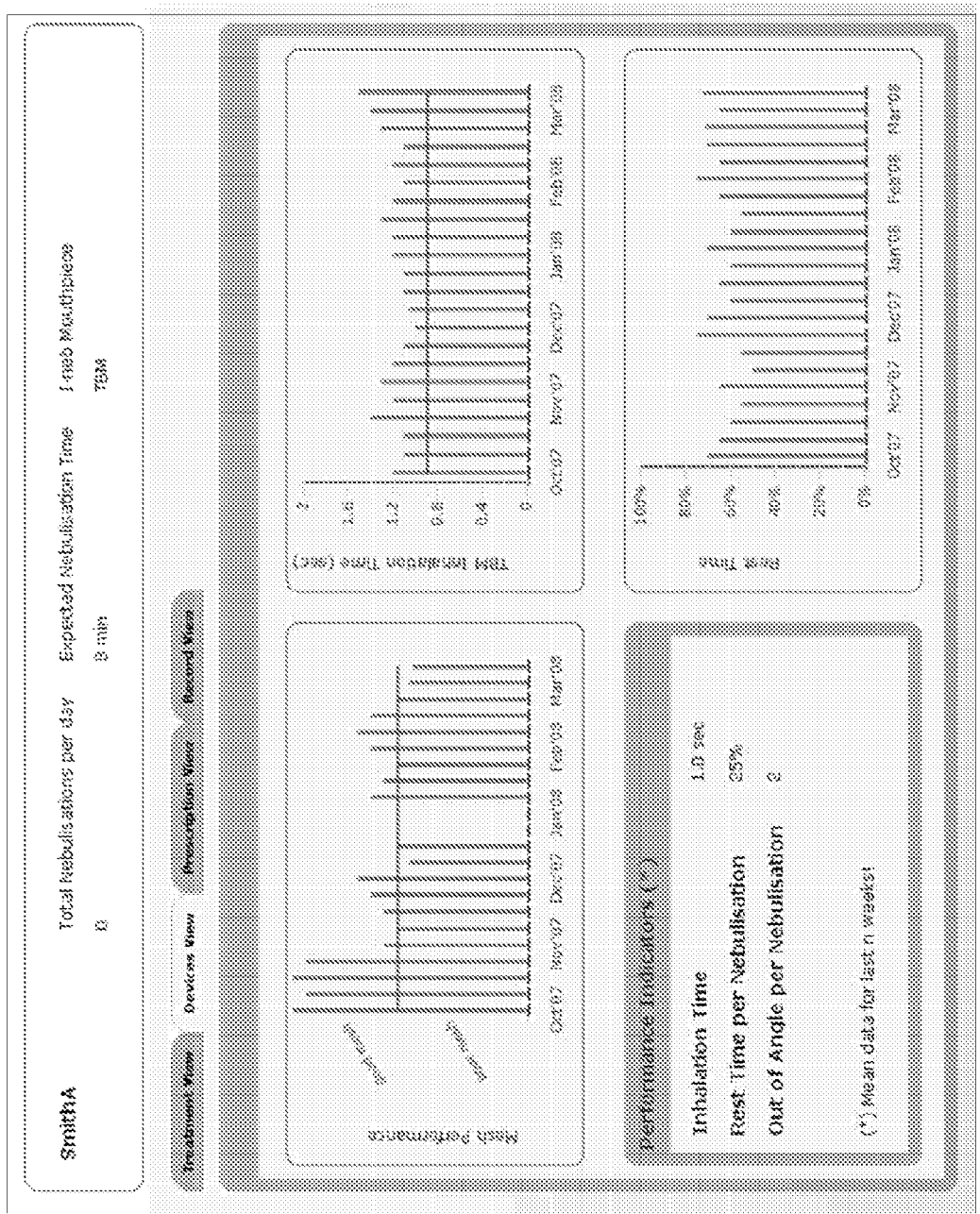
FIG. 7 illustrates a device view of a user interface that provides information to a user about the performance of a drug delivery device according to various aspects of the invention.

Similarly, FIG. 7 illustrates an embodiment of the user interface defined by user interface module 282 in which the user interface includes a view that presents therapy information to the user related to the performance of a drug delivery device used by a patient or group of patients. This view may be referred to as a "device view." The device view includes information related to metrics that quantify drug delivery device performance. This type of information is discussed further below.

Other views that may be included in the user interface may include one or more of a prescription view, a record view, a patient grouping view, and/or other views. The prescription view includes information related to the therapy regime that has been prescribed for a patient or group of patients. The record view includes information related to historical device usage and/or respiratory function of a patient or group of patients. The patient grouping view enables the user to view, create, and/or manipulate groupings of patients. The patient groupings may be established based on one or more of demographic information (e.g., age, ethnicity, sex, geographic location, education, socioeconomic classification, and/or other demographic information), medical condition, medicament received, therapy regime prescribed, and/or other information. This grouping may be done manually by the user and/or automatically by server 272.

Returning to FIGS. 2-I and 2-II, user interface module 282, in one embodiment, generates a definition of a user interface that provides one or more views to the user that enable one or more parameters of the treatment regime prescribed for a patient or group of patients to be adjusted by the user. Adjustments entered through the user interface defined by the definition generated by user interface module 282 are then provided to the appropriate drug delivery device (e.g., drug delivery device 100 and/or drug delivery device 288) via server 272.

The communications module 284 is configured to provide the definition of the user interface generated by user interface module 282 to the user. In one embodiment, communications module 284 accomplishes this by serving the user interface to a client computing platform 292 associated with the user. The client computing platform 292 may include one or more of a laptop computer, a desktop computer, a netbook, a smartphone, and/or other client computing platforms. The communications module 284 may serve the user interface to client computing platform 292 over a network. This network may include the Internet and/or an intranet associated with a clinic (or set of clinics), a hospital (or set of hospitals), or other entities. In order to view the defined user interface, client computing platform 292 may implement a versatile client application, like a web browser, to render the user interface based on the communication from communications module 284. As was mentioned above, in one embodiment, rather than a versatile client application like a web browser, client computing platform 292 may execute a client application that is specifically designed for viewing the user interface defined by definitions generated by user interface module 282.

In one embodiment, the user interface defined the definition generated by user interface module 282 enables the user to input communication directed toward a patient or group of patients. This communication is then distributed by communications module 284 to the patient or group of patients. The communication may be distributed to the patient or group of patients via their drug delivery devices (e.g., via drug delivery device 100 by way of client computing platform 274), via one or more client computing devices associated with the patient or group of patients, and/or via other communication devices associated with the patient or group of patients (e.g., via SMS message, via voicemail, via automated phone call, etc.). These communications may include messages selected by the user from a predefined set of communications indicating action that the patient or group of patients should with respect to their drug delivery device(s), adjustments that should be made to the treatment regime prescribed for the patient or group of patients, adjustments that should be made by the patient or group of patients to respiration during treatment, and/or other messages. The user interface may present a set of communications to the user based on analysis of therapy information obtained by therapy information acquisition module 280.

In one embodiment, communications module 284 further enables patients to transmit communications back to the user. For example, communications module 284 may be configured to receive communications input by a patient to drug delivery device 100 and/or client computing platform 274, and to provide such communication to the appropriate user (e.g., via client computing platform 292). These communications may be in response to communications received from the user (e.g., confirming a change and/or action indicated in a communication from the user has been made and/or taken), or may be instigated entirely by the patient.

The therapy parameter module 285 is configured to determine one or more parameters of the therapy regime prescribed for the patient. As will be discussed further below. These parameters may be determined based on therapy information acquired during previous therapy sessions. One or more of the parameters may be determined on the actual drug delivery devices (as discussed below). Previously determined parameters, whether determined on the drug delivery devices and/or by therapy parameter module 285, may be presented to the user via the user interface defined by user interface module 282. The user interface may enable the user to adjust at least one of these parameters. The adjusted parameters and/or parameters determined by therapy parameter module 285 may be communicated to the drug delivery devices (e.g., to drug delivery device 100 via client computing platform 274) by communications module 284.

The update module 286 is configured to effectuate the update of software associated with the therapy received by patients via drug delivery device 100 and/or drug delivery device 288. This may include software stored and executed on client computing platform 274 and/or client computing platform 290, and/or software stored and executed on drug delivery device 100 and/or drug delivery device 288. Update module 286 effectuates such updates by pushing electronic information including the updates to the appropriate devices and/or machines over the communications network(s) through which server 272 obtains therapy information from drug delivery device 100 and/or drug delivery device 288. Control over this transmission of update information may be controlled by the user via client computing platform 292.

It will be appreciated that enabling communication between server 272 and devices (e.g., drug delivery device 100, drug delivery device 288, client computing platform 274 and/or client computing platform 290) associated with individual patients provides various enhancements over previous systems. For example, the communication of therapy information associated with the different patients to a centralized entity (the server 272) provides users with centralized, convenient access to information needed to monitor and/or manage a plurality of disparate patients and/or drug delivery devices. Similarly, enabling a user to generate customized communication from the centralized entity to the individual patients facilitates a superior treatment experience for the patients. Further, the functionality provided by update module 286 may provide time and/or money savings over systems in which updates to software must be individually distributed through conventional channels and then individually installed manually by the patients.

In one embodiment, the users that are able to access therapy information via server 272 includes the actual patients receiving the therapy, not just caregivers, researchers, etc. In this embodiment, rather than executing a "thick" client application on client computing platform 274 and/or client computing platform 290 to monitor therapy, the patients may access therapy information from server 272 using a "thin" client application (like a web browser). This may reduce the costs associated with setting up and/or maintaining the system illustrated in FIGS. 2-I and 2-II because it would remove costs associated with distributing, installing, maintaining, and updating specialized software on client computing platforms associated with the patients (e.g., client computing platform 274 and/or client computing platform 290).

Figure 3:
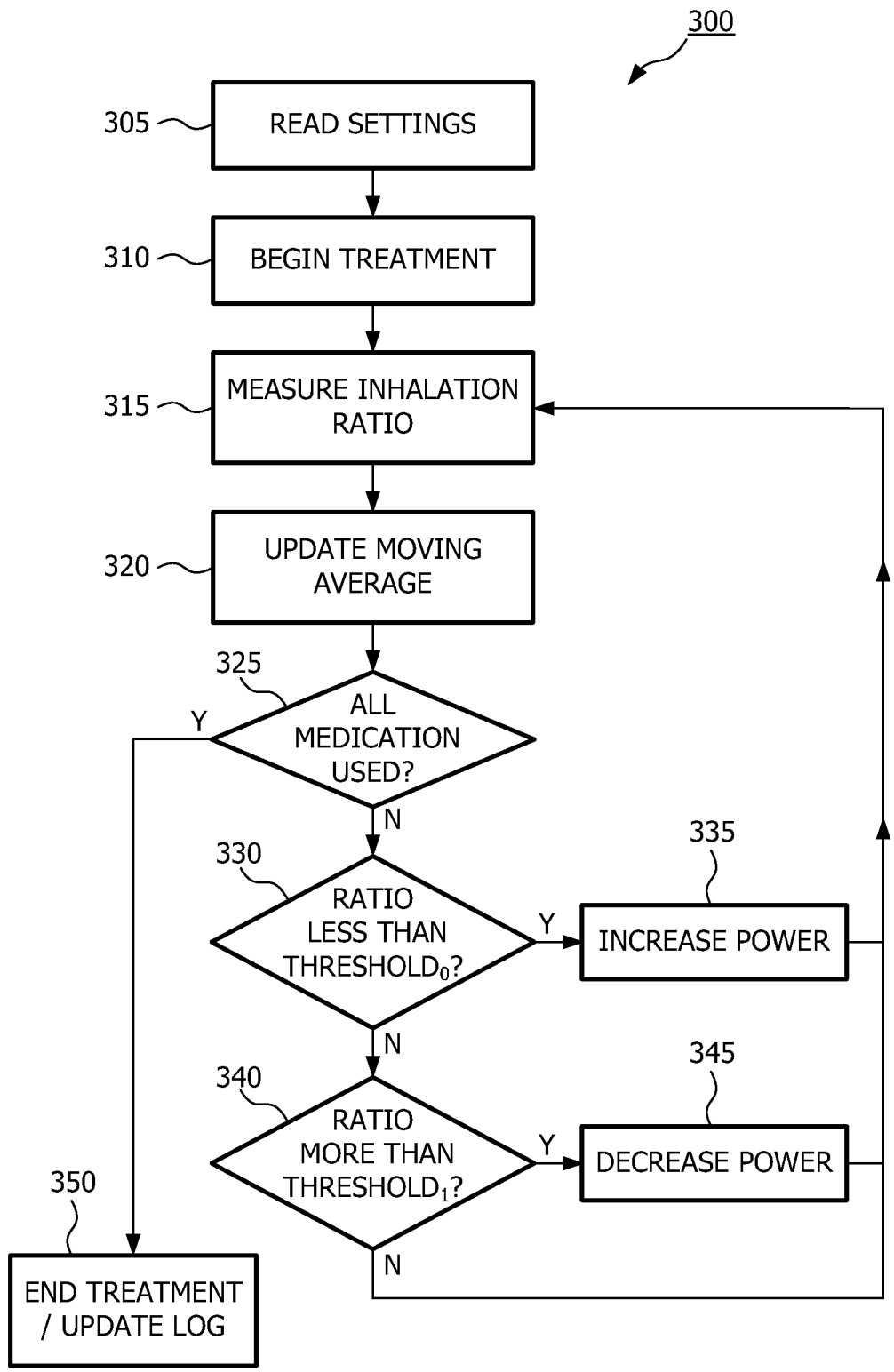
FIGS. 3-4 illustrate exemplary methods for maintaining consistency for aerosol drug delivery treatments according to various aspects of the invention.

Referring to FIG. 3, an exemplary method 300 for maintaining consistency for aerosol drug delivery treatments is illustrated. Method 300 may be used to vary a power level of aerosol drug delivery device 100 during treatment to maintain a consistent time for the treatment. For example, treatment duration may depend on a patient's breathing pattern, and method 300 may vary the power level in response to the breathing pattern to maintain a consistent treatment time, as described in greater detail below.

As an initial operation, one or more settings may be read at operation 305 (e.g., from settings stored in data repository 260, or otherwise) to initialize an aerosol drug treatment. Alternatively, the settings may be input manually into the data repository 260 or other memory in the drug delivery device 100. In one embodiment, one or more of the settings may be provided to data repository 260 from server 272 (e.g., via client computing platform 274) in accordance with a therapy regime defined for the patient by a user (e.g., the user interface provided on client computing platform 292). The settings may include information relating to the treatment, including a dosage of drug for the treatment (e.g., dependent on a quantity of drug in a medication chamber of the drug delivery device or physical volume of the reservoir 115), a target treatment duration, a mesh grading, and a nominal power level, among other things. As such, the therapy information may be used to calculate a nominal output rate (e.g., milliliters per minute) and a target pulse proportion (e.g., a proportion of each minute to be spent delivering aerosol pulses) for the aerosol drug treatment. Moreover, the settings read in operation 305 may include parameters for varying the power level during the treatment, including, among other things, minimum and maximum power levels, threshold inhalation to exhalation ratios for triggering changes in power levels, and variables for indicating how much to increase and/or decrease the power levels in any iteration.

Having all parameters and settings for administering and controlling treatment, input into, or otherwise stored or contained in, the data repository 260 or other memory, the treatment may begin at operation 310. When the treatment begins at operation 310, the power level delivered by power source 220 to the aerosol generator 120 may be set to the nominal power level. In various implementations, however, the nominal power level may be subject to variation based on therapy information from data repository 260 relating to one or more previous treatments. For example, when a patient exhibits a poor breathing pattern (e.g., by spending comparatively less time inhaling than normal), the nominal power setting may be increased to account for treatment otherwise likely to extend beyond the nominal treatment time. Other variations may be used, such as decreasing the nominal power setting when a patient has a longer than normal inhalation pattern, or otherwise, as will be apparent.

Over a course of the treatment, a patient's breathing pattern may be actively monitored. For instance, operation 315 includes measuring the patient's inhalation to exhalation ratio on a breath-by-breath basis, while operation 320 includes updating the running moving average of the inhalation ratio to reflect a most recent breath. Thus, the power level of the aerosol generator 120 may be dynamically adjusted for each breath, on a breath-by-breath, basis in response to any changes that occur to the breathing pattern. The change for any one breath may be based on a single prior breath, or on a plurality of prior breaths. In another embodiment, the power level of the aerosol generator 120 may by dynamically adjusted for a predetermined number of future breaths, based on only the preceding breath, or based on a plurality of prior breaths. In one embodiment, treatment time may be dependent upon a proportion of every minute that the aerosol generator 120 delivers aerosol pulses, which may further depend on a ratio of time that the patient spends inhaling versus exhaling. The inhalation to exhalation ratio may have a substantial effect on treatment time because a length of each pulse may be keyed to the ratio.

Each aerosol pulse may begin when an inhalation begins, or shortly thereafter (e.g., within one second from when inhalation begins), while ending prior to when the inhalation ends, thus leaving a period of time for the aerosol to deposit in the patient's body. As such, in one embodiment, the pulse length may last between approximately fifty and eighty percent of an inhalation, depending on the ratio (e.g., a patient that takes many short inhalations may receive proportionally shorter pulses and more deposit time than a patient that takes long inhalations). Exemplary techniques for controlling the pulse length based on breathing pattern may include those described in the '971 patent.

Accordingly, an inhalation to exhalation ratio may be a significant factor affecting treatment duration, as the treatment may be longer for patients having comparatively low inhalation to exhalation ratios, and vice versa. Thus, consistent treatment times may be maintained by increasing power levels delivered to aerosol generator 120 to compensate for a patient having a poor breathing pattern, or decreasing power levels delivered to aerosol generator 120 to compensate for a patient having a strong breathing pattern, ensuring that a quantity of aerosol generated per minute remains close to the desired nominal output rate.

Throughout the treatment, operation 320 may maintain a running moving average of the inhalation to exhalation ratio. The ratio may be measured by the controller 230 in conjunction with the breath measuring mechanism 245, and a moving average of the ratio, measured over a predetermined number of breaths (e.g., three breaths) may be determined by the controller 230 and stored in data repository 260 or other memory in the drug delivery device. For example, in various implementations, the moving average may be based on a limited number of breaths to ensure the moving average reflects a current breathing pattern. As various examples, a patient may experience an asthmatic attack during treatment, or drug absorption may improve a patient's respiratory strength, or other variations may occur such that the current breathing pattern may change dynamically over the course of treatment. As such, limiting a number of breaths factoring into the moving average may result in a more accurate assessment of the current breathing pattern. It will be apparent, however, that the number of breaths may be suitably increased or decreased when appropriate, or certain treatment types may include all breaths in the moving average without departing from the scope of the invention.

In operation 325, a determination is made as to whether all medication in the reservoir 115 has been administered. For example, in various implementations, the sensor 217 can detect the presence (or absence) of liquid in the reservoir 115. The sensor 217 may comprise any device for measuring the presence or absence of liquid, or the amount of liquid, in the reservoir 115. For example, a light obstruction or scattering sensor, an ultrasound or radio wave transmission time sensor, a sensor that measures electrical capacitance of air, a float switch, or other known sensors that can detect the presence of or absence of liquid can be used. In another embodiment, the sensor 217 may be constructed and arranged to determine changes in characteristics (e.g., changes in current or voltage) of an ultrasonic drive circuit for driving the horn or aerosol generator 120, where the changes are attributable to the depletion of the liquid from the reservoir 115.

As described in the incorporated '971 patent, the sensor 217 can be used to determine when the treatment should end (e.g., by detecting the absence of liquid in the reservoir 115). When all medication in the reservoir 115 has been administered, as determined by the sensor 217, this means that the prescribed dosage of drug has been administered, and the sensor 217 may send a signal to the controller 230 to indicate that treatment can be terminated in operation 350 (e.g., by cutting power to the aerosol generator 120). Further, operation 350 may update a log or generate a record of the treatment in data repository 260 for further analysis or diagnosis, among other things, as described in greater detail below.

However, when determination operation 325 determines that additional medication remains to be administered (e.g., when the sensor 217 detects the presence of additional medication in reservoir 115), treatment will continue, while inhalation/exhalation ratio determinations 330 and 340 determine whether to increase and/or decrease the power level (at operations 335 or 345) in subsequent pulses. For example, the inhalation/exhalation ratio determinations made in operations 330 and 340 may be based on a breathing model reflecting a typical patient inhalation to exhalation ratio, varying between approximately 1:1 and 1:2 (i.e., some patients may spend twice as much time exhaling as other patients in proportion to inhalation time).

As such, when it is determined at operation 330 that the proportion of inhalation time to exhalation time has fallen below a first threshold (i.e., $Threshold_0$ reflecting a poor breathing pattern), through use of the breath measurement mechanism 245, the power level may be increased at operation 335 by a first delta. By contrast, when the inhalation/exhalation time proportion has not fallen below $Threshold_0$ but exceeds a second threshold (i.e., $Threshold_1$ reflecting a strong breathing pattern), the power level may be decreased at operation 345 by a second delta. For example, the power level may be increased or decreased via power controller 235, which may provide an electronic signal to power source 220 that regulates the power level delivered to aerosol generator 120. In various implementations, $Threshold_0$ and $Threshold_1$ may be based on any suitable model, and the first delta may be set to be larger than the second delta to reflect a poor breathing pattern having a greater impact on treatment time than strong breathing patterns. Otherwise, the breathing pattern may reflect typical inhalation to exhalation ratios, in which case processing returns to operation 315 without changing the power level, awaiting another breath to measure.

Furthermore, power levels may be constrained within an appropriate range, defined by a predetermined minimum level and a predetermined maximum level. The minimum level may be defined to ensure that power continues to be delivered to the aerosol generator 120 as long as medication remains in the reservoir 115 (e.g., the minimum level may ensure that the device does not turn off, or that power does not go to zero). Similarly, the maximum power level may be defined to ensure that power circuitry does not become overloaded or otherwise interfere with proper operation of the device. Specific power levels may depend on a design or configuration of any given device, which is manufactured to have a maximum power output.

Upon sensor 217 determining that all medication has been used, thereby ending the treatment at operation 350, the log in data repository 260 may be updated in that operation 350. The log in data repository 260 may store information about each treatment administered for a patient. The stored therapy information may be downloaded to server 272 and/or client computing platform 274, and may include, for each treatment, a total aerosol generator (e.g., a horn) actuation time, a total amount of time the patient spent inhaling, and a total amount of time the patient spent exhaling, among other things. In various implementations, one or more of the horn actuation time, the inhalation time, or the exhalation time may be rounded to a nearest second.

The therapy information transferred to server 272 from data repository 260 may be used to aid therapists in assessing diagnostics of a patient's treatment or to otherwise provide additional understanding regarding treatment. For example, the time spent inhaling and/or exhaling during treatments may be used to diagnosis a patient's breathing. Moreover, the therapy information may provide an indication of how actively power levels were varied during treatment to compensate for breathing patterns. For example, a proportion of time spent inhaling may be calculated (e.g., by dividing the time spent inhaling by the sum of the time spent inhaling and exhaling) to analyze breathing patterns and power changes, where a proportion of less than about forty percent may indicate that power was actively increased during various breaths, a proportion of between about forty percent and about forty-eight percent may indicate that power was subject to minimal net effects, and a proportion of greater than about forty-eight percent may indicate that power was actively decreased during various breaths. It will be appreciated, however, that these percentages and ranges thereof are exemplary only and can be varied for all patients, or on a patient-by-patient basis, or otherwise. Further still, the log may store codes used to provide feedback to the patient when a treatment has completed. For example, various codes may indicate whether the patient's breathing pattern during the treatment was normal, poor, strong, or otherwise (e.g., by displaying on a display connected to controller 230, an indication of the patient's breathing pattern based on the proportion of time spent inhaling and/or exhaling).

In one embodiment, any of this information that may help a physician diagnose a patient may be sent by the controller 230 to a display 270 on drug delivery device 100 and/or client computing platform 274. The display 270 may be a liquid crystal display, a light emitting diode (LED) display, or other readable display. In another embodiment, the display 270 can be replaced by any device capable of providing a perceptible output. For example, a speaker can be used to provide an audible alert that may output a sound or voice recorded message diagnosing a certain condition (e.g., "poor breathing pattern").

Figure 4:
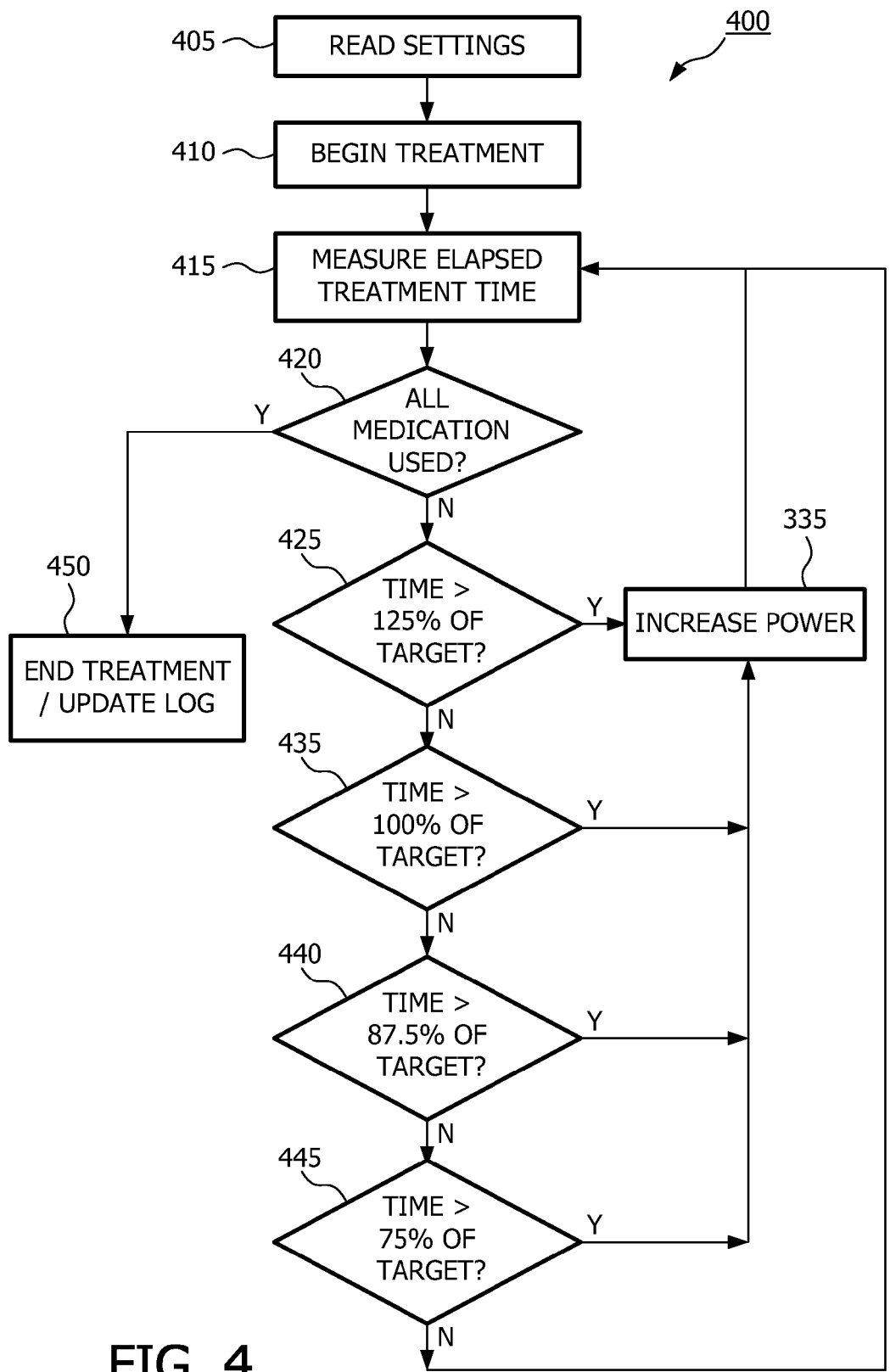

Referring to FIG. 4, another method 400 for maintaining consistency for aerosol drug delivery treatments is illustrated according to various aspects of the invention. Method 400 may be used to vary a power level delivered to the aerosol generator 120 during treatment to maintain a consistent time for the treatment. For example, a nominal treatment duration may depend on a nominal output rate for an aerosol drug delivery device (e.g., a function of mesh grading, drug dosage, and nominal power level). As such, method 400 may monitor an elapsed duration of a treatment at procedure 415, and may slowly increase the power level as a function of the nominal treatment time. Thus, method 400 may maintain the output rate as close as possible to the nominal rate, thereby achieving a consistent treatment time.

Beginning the method 400, one or more settings may be read at operation 405 (e.g., from settings stored in data repository 260, whether preselected, manually input, received from server 272, etc.) to initialize an aerosol drug treatment. The settings may include information relating to the treatment, including a dosage of drug for the treatment (e.g., dependent on a total fill volume of the medication reservoir 115 (a preselected fixed volume), or input based upon a quantity of drug (the dose) actually placed in medication reservoir 115 of the drug delivery device 200), a target treatment duration, a mesh grading, and a nominal power level, among other things. Again, any one or more of the settings may be manually input to data repository 260 through an input interface, received at data repository 260 from server 272, or may be pre-coded into the data repository 260. As such, the therapy information may relate to a nominal output rate (e.g., milliliters per minute) and a target pulse proportion (e.g., a proportion of each minute to be spent delivering aerosol pulses). As discussed above, in various instances a dirty mesh or an interchanging of meshes may cause an actual device output rate to vary from the nominal output rate.

Having the parameters and settings for administering and controlling treatment read at operation 405, the treatment begins at operation 410. After the treatment begins, an elapsed time of the treatment may be monitored at operation 415 (e.g., via clock 250). In addition, at operation 405 the power level delivered to the aerosol generator 120 may initially be set to the nominal power level (e.g., based on the read settings, or a manual input, a reactive mechanism based on previous treatments, etc.). By determining the nominal treatment duration when the settings are read at operation 405, the power level to the aerosol generator 120 may be increased when a treatment appears likely to exceed the target duration, thus compensating for a fall in device output rate. For example, whether or not all medication is used is determined at operation 420. If operation 420 determines (through sensor 217) that the reservoir 115 contains medication that must still be administered, and the elapsed time approaches the target treatment duration, it may be assumed that the device output rate has fallen below the nominal rate, or may potentially be below the nominal output rate (e.g., because of a dirty mesh). Rather than waiting for the elapsed time to pass the nominal treatment duration, however, the power level may be increased (at step 430 as discussed below), or otherwise ramped up slowly in advance of the treatment ending. As a result, when the mesh is dirty or otherwise functioning less than optimally, the treatment time can end in close proximity to the desired or nominal time, or at least closer to the nominal time in comparison with no increase in power supplied to the aerosol generator 120.

Accordingly, operation 445 increases the power if the elapsed time reaches 75% of nominal treatment time, operation 440 increases the power if the elapsed time reaches 87.5% of nominal treatment time, operation 435 increases the power if the elapsed time reaches 100% of nominal treatment time, and operation 425 increases the power if the elapsed time reaches 125% of nominal treatment time. Thus, the power level slowly increases towards the end of a treatment based on a relationship between elapsed treatment time and nominal treatment time. It should be appreciated, however, that the specific intervals illustrated herein are exemplary only, and that the selected intervals may be varied, or additional intervals may be substituted, as appropriate (e.g., the number of intervals could be doubled by halving the degree by which the power is increased). In one embodiment, drug delivery device 100 may include a predetermined number of power levels, and an output rate of the device may be a function of the power level. Accordingly, by increasing and/or decreasing the power level by a given amount, the output rate of the device can be controlled. In an exemplary illustration, the drug delivery device 100 may include a range of power levels as indicated in the following table, where each power level provides a device output rate that is a function of a default power level (e.g., level 8 in the illustrated table).

| Power Level | Percent Change in Output Rate from Default Power Level (e.g., Level 8) |
| --- | --- |
| 1 | 45.8% |
| 2 | 53.5% |
| 3 | 61.3% |
| 4 | 69.0% |
| 5 | 76.8% |
| 6 | 84.5% |
| 7 | 92.3% |
| 8 | 100% |
| 9 | 107.7% |
| 10 | 115.5% |
| 11 | 123.2% |
| 12 | 131.0% |
| 13 | 138.7% |
| 14 | 146.5% |
| 15 | 154.2% |

In another embodiment, rather than increasing the power to the aerosol generator 120 at predetermined intervals, it is contemplated that the power level may be increased continuously over time, either linearly or exponentially, starting at a predetermined percentage of the nominal treatment time. In another embodiment, the increase in power commences at a derived time, rather than a predetermined time. Such derived time for increasing power may be based on prior measurements or determinations of how long it has taken the fill dose of medicament in the reservoir 115 to be depleted, as determined by sensor 217. These past measurements of reservoir depletion time may be stored in data repository 260 and/or server 272 to determine the start time for increasing the power to aerosol generator 120, the rate at which power is increased, and/or the total duration of increase in power.

Upon determining that all medication has been used (e.g., by the sensor 217 detecting that all medication has been administered), the sensor 217 will send a signal to the controller 230, which in turn will send a signal to turn off power source 220. Thus, at operation 450 the treatment will end and the log in data repository 260 may be updated. The data repository 260 may store information about each treatment administered for a patient. The stored information in data repository 260 may be downloaded to a personal computer or other suitable device with a readable and writable memory. The information stored in the repository 260 may include, for each treatment, a total amount of actuation time of aerosol generator 120, a total amount of time spent inhaling by the patient, and/or total amount of time spent exhaling by the patient, among other things. In various implementations, one or more of the drug delivery actuation time (i.e., actuation time of the aerosol generator device or horn), the inhalation time, or the exhalation time may be rounded to a nearest second, for example.

As previously noted, the controller 230 may be used to perform various diagnostics for the patient or the device 200, which may be presented to the patient via a display 270. Similarly, such diagnostics may be provided to a user of the system illustrated in FIGS. 2-I and 2-II via client computing platform 292. For example, when the therapy information within data repository 260 and/or server 272 indicates that mesh 105 may be dirty, the display 270 may be caused (e.g., via instructions received from controller 230 and/or server 272) to visually depict the need to change the dirty mesh 105. In another example, the display 270 may be caused to provide a visual indicator when the therapy information indicates that the patient has a poor breathing pattern, such that the patient can follow up with a medical practitioner or take other appropriate action. In yet another example, a warning or indication of the probable state of the mesh may be conveyed to a user via client computing platform 292, and communication may be input by the user to client computing platform 292 that is conveyed to the patient via server 272 that instructs the patient to clean and/or replace the mesh.

Furthermore, the therapy information in the data repository 260 and/or server 272 may be used to perform various analytics or calculations to control subsequent treatments. For instance, treatment lengths may be calculated by controller 230 and/or server 272 for a current treatment and/or one or more previous treatments, and the power level may be varied for subsequent treatments based on the calculations (e.g., an initial power level may be varied based on calculations from one or more previous treatments, or the calculations may be used to derive a schedule for controlling or otherwise varying the power level during a treatment, or other techniques may be used).

Information determined by server 272 and/or received from controller 230 on server 272 may also be used to aid therapists in assessing diagnostics of a patient's treatment, or to otherwise provide additional understanding regarding treatment, including whether poor mesh conditions necessitate interchanging of the mesh, or whether suitable mesh conditions indicate that the mesh can be changed later, among other things. For example, the therapy information in the data repository 260 may include information relating to the nominal mesh output rate (e.g., milliliters per minute) and medication chamber dose or volume (e.g., milliliters), which can be used to calculate a nominal amount of actuation time for a aerosol generator 120 at the nominal rate for a given treatment. For instance, a treatment may be designed to administer 6000 mL of medication at a nominal rate of 1000 mL/min (i.e., a six-minute treatment). Thus, the nominal amount of actuation time may be based on how many seconds the aerosol generator 120 (e.g., horn) should have been actuating during any given minute of the treatment.

As such, the total amount of nebulizer actuation time (e.g., horn-on time, or HOT) for each treatment may be compared to the nominal actuation time (e.g., nominal horn-on time, or nHOT), thereby providing an indication of whether the treatment was longer than expected because of a dirty mesh. Data may be further analyzed or correlated with subsequent treatments to reveal trends in mesh conditions (e.g., the trend may indicate that the mesh frequently becomes dirty after three uses, providing an estimate for when the mesh should be changed). Furthermore, treatment duration, in itself, may not provide an adequate measure of a dirty mesh because the duration does not account for influences attributable to a patient's breathing pattern, or to time spent not breathing (e.g., in between breaths), or other factors. Thus, dirty mesh conditions may be determined based on HOT as a percentage of nHOT (e.g., by dividing HOT by NHOT), or other factors, as HOT will only be affected by dirty mesh conditions or other factors that impact device output rate. For example, when the percentage HOT divided by NHOT exceeds a predetermined value (e.g., 200%), a dirty mesh can be assumed because increasing the power at the end of treatment failed to yield a treatment time within acceptable ranges, indicating that the mesh should be cleaned or changed. As will be apparent, the indication may be displayed on display 270 visually to indicate the need to clean or interchange the mesh.

Based on the foregoing, it will be apparent that a treatment may extend beyond the target treatment time because of a poor patient breathing pattern or because of a dirty mesh or other factor contributing to a reduction in device output rate. As such, the method described in FIG. 4 may actively monitor and compensate the breathing pattern, such that a treatment extending beyond the target treatment time may be attributable to the reduction in device output rate, which may be compensated for using the method described in FIG. 4. Therefore, either one or both of methods 300 and 400 may be active for any given treatment to compensate for these various factors, and which of the methods will be active may depend on settings of the device. It should be noted that controlling the power level based on patient breathing pattern in accordance with method 300 may be universally enabled for any aerosol treatment device, whereas controlling the power level to compensate for dirty mesh conditions in accordance with method 400 is primarily intended to be used with drug delivery devices that employ a mesh or other component that may deteriorate over time to thus cause a reduction in device output rate. It will also be appreciated that the settings may be based on any number of factors, or that a button or other selection mechanism could be used to enable/disable the power control algorithms, or other techniques may be used.

Further, in various embodiments, when simultaneously activating methods 300 and 400 for a treatment, method 300 will automatically terminate at a predetermined percentage (e.g., seventy-five percent) of the target treatment duration. In such a case, method 400 would take precedence over method 300 at that time. This is because method 300 dynamically accounts for variables relating to breathing pattern throughout the initial portion (e.g., the first seventy-five percent) of the treatment. Therefore, when the elapsed treatment duration exceeds the predetermined percentage of the target treatment duration (e.g., because the liquid drug has not been completely dispensed by that time), a dirty mesh can be assumed as being the reason for the longer treatment (e.g., exceeding target treatment duration can be attributed to a reduction in device output rate). As described above, ramping power up at the end of treatment should begin in advance of the treatment ending (e.g., to gradually increase the drug to be inspired), and therefore, method 400 will take precedence beginning at the predetermined percentage (e.g., seventy-five percent) of the target treatment duration.

Figure 5:
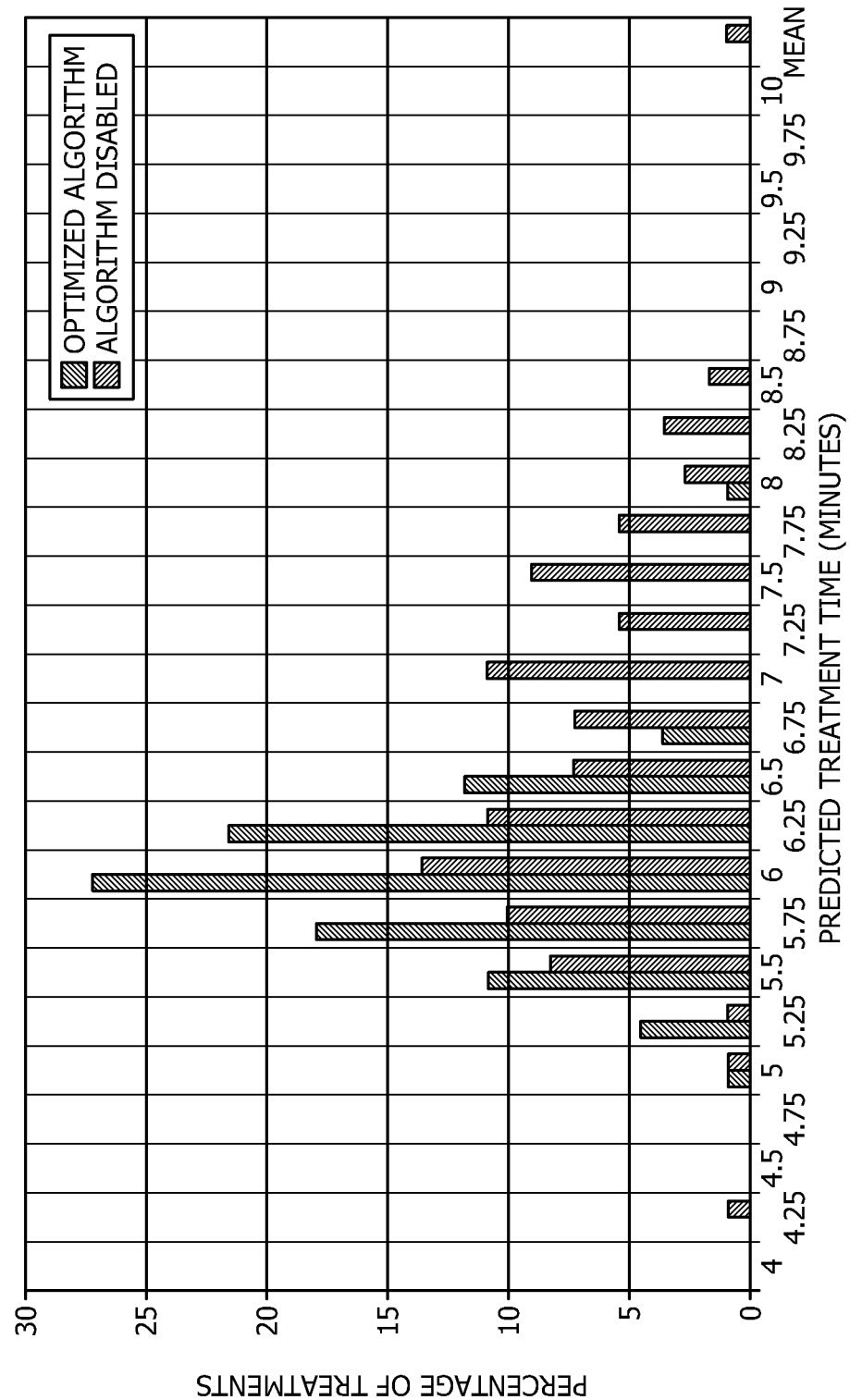
FIG. 5 illustrates a histogram comparing distributions of treatment times as a function of using a variable power algorithm according to various aspects of the invention.

Referring to FIG. 5, a histogram illustrates a comparison of distributions of treatment times as a function of using a variable power algorithm versus disabling the variable power algorithm. The histogram illustrated therein is based on experimentation using a database of approximately one hundred ten different breathing patterns. Based on a target treatment time of six minutes, when disabling the variable power algorithm, treatment times ranged from approximately four minutes, 15 seconds to eight minutes, thirty seconds (with a small percentage of treatments exceeding ten minutes). The mean treatment time with the variable power algorithm disabled was approximately 6.5 minutes, with a standard deviation of fifty-six seconds. By contrast, using the optimized variable power algorithm, most treatments completed between five minutes and six minutes, thirty seconds (with a small percentage exceeding six minutes, thirty seconds). As such, the variable power algorithm can be expected to significantly reduce the variability of treatment times and reduce mean treatment times of a representative population of patient breathing patterns. In particular, with the variable power algorithm enabled, the mean treatment time was reduced to approximately 5.9 minutes (a seventeen percent reduction), while the standard deviation was reduced to approximately twenty-four second (a fifty-seven percent reduction).

In another embodiment, the power may be adjusted based on a variety of other measured parameters other than those described above. For instance, sensor 217 may be configured to directly determine the liquid level within the reservoir 115 rather than for simply detecting treatment completion. Data repository 260 and/or server 272 may include a table of values or calculator to determine the current desired liquid level to achieve a desired total delivery time. The current detected liquid level and the current desired liquid level at a given time may then be compared. If the current detected liquid level is less than the current desired liquid level, the power may be decreased. If the current detected liquid level is greater than the current detected liquid level, the power may be increased. The sensor 217 may have a variety of configurations; however, the present invention contemplates that sensor 217 may be a ultrasonic transducer configured to detect impedance changes, a resistive circuit configured to detect changes in resistance and/or current, a float switch, or any other liquid level detector known in the art. Alternatively, the liquid level may be inferred based on the amount of aerosol delivered to the patient. The amount of aerosol output from the drug delivery device 100 to the patient. For instance, the amount of liquid consumed may be determined by summing the concentration of aerosol output from the device over the delivery time period. The concentration sensor may be an optical concentration sensor, a particle sensor, or any other suitable concentration sensor known in the art.

Figure 8:
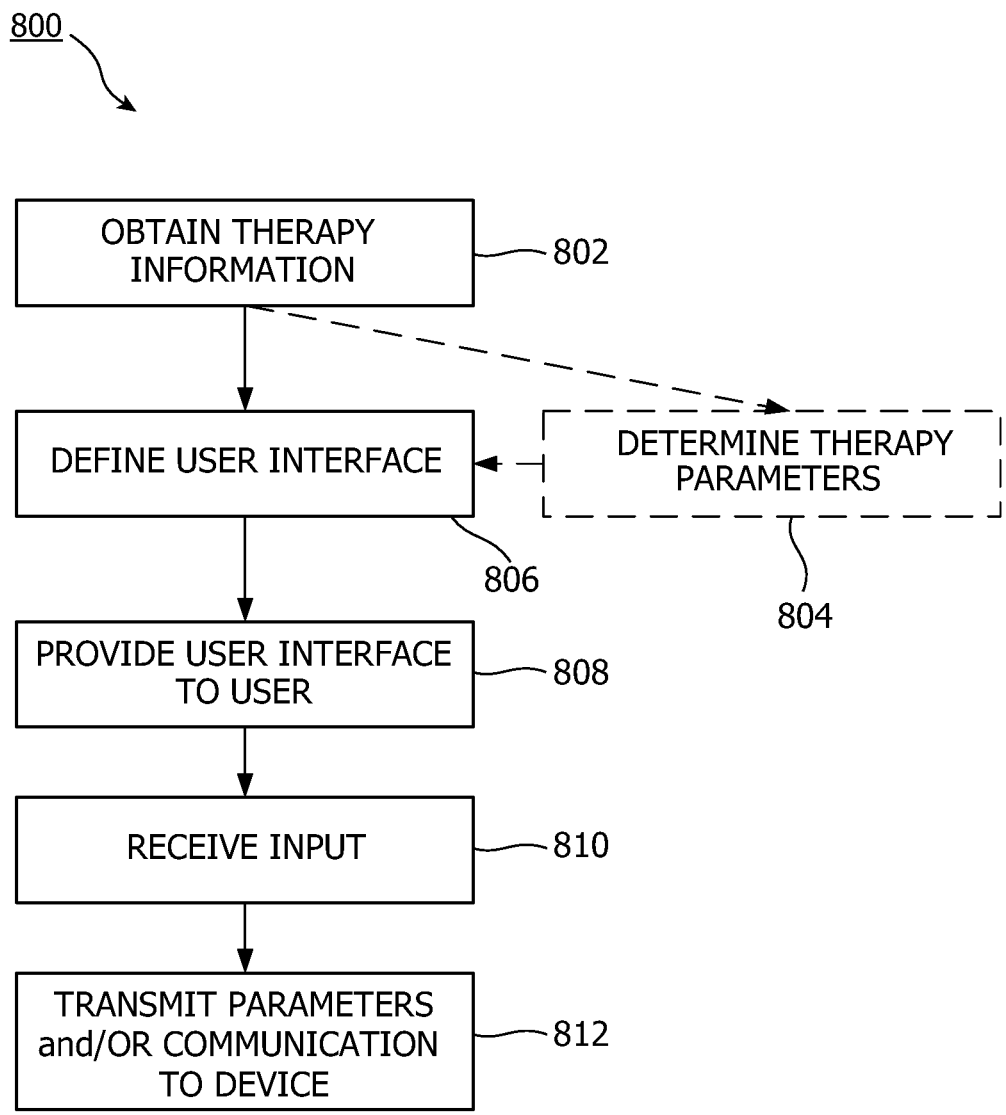
FIG. 8 illustrates a method of monitoring the therapy received by a plurality of subjects.

FIG. 8 illustrates a method 800 of enabling one or more users to monitor therapy of a plurality of subjects remotely, wherein such therapy includes the delivery of aerosolized medicament. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented by a server including one or more processing devices (e.g., a digital processor, an analog processor, a digital circuit designed to process information, an analog circuit designed to process information, a state machine, and/or other mechanisms for electronically processing information) configured to execute one or more computer program modules. The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, therapy information from a plurality of drug delivery apparatuses are obtained over a communications network. The plurality of drug delivery apparatuses include a first drug delivery apparatus associated with a first subject and a second drug delivery apparatus associated with a second subject. The first drug delivery apparatus and the second drug delivery apparatus may be the same as or similar to drug delivery device 100 and/or drug delivery device 288 (shown in FIGS. 2-I and 2-II and described above). The therapy information includes information related to breathing patterns of the first subject and the second subject, and/or information related to the efficiency or performance of one or more components of the first drug delivery device and the second drug delivery device (e.g., a mesh used to aerosolize medicament). In one embodiment, operation 802 is performed by a therapy information acquisition module that is the same as or similar to therapy information acquisition module 280 (shown in FIGS. 2-I and 2-II and described above).

At an operation 804, one or more parameters of therapy regimes prescribed for the individual subjects are determined. The one or more parameters are determined based on therapy information obtained at operation 802. In one embodiment, operation 804 is performed by a therapy parameter module that is the same as or similar to therapy parameter module 285 (shown in FIGS. 2-I and 2-II and described above).

At an operation 806, a user interface is defined for a user that enables the user to selectively view therapy information obtained at operation 802 and/or the parameters determined at operation 804. In one embodiment, operation 806 is performed by a user interface module that is the same as or similar to user interface module 282 (shown in FIGS. 2-I and 2-II and described above).

At an operation 808, the user interface defined at operation 806 is provided to the user. In one embodiment, operation 808 is performed by a communications module that is the same as or similar to communications module 284 (shown in FIGS. 2-I and 2-II and described above).

At an operation 810, communication for one or more subjects and/or one or more therapy parameters are received from the user via the user interface provided to the user at operation 808. In one embodiment, operation 810 is performed by a communications module that is the same as or similar to communications module 284 (shown in FIGS. 2-I and 2-II and described above).

At an operation 812, communications and/or parameters are provided received at operation 810 are provided to the appropriate subject(s). In one embodiment, operation 812 is performed by a communications module that is the same as or similar to communications module 284 (shown in FIGS. 2-I and 2-II and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to enable one or more users to monitor therapy of a plurality of subjects, wherein such therapy includes the delivery of aerosolized medicament, the system comprising:
    server comprising one or more processors configured to execute one or more computer program modules, the one or more modules comprising:

a therapy information acquisition module configured to obtain, over a communications network, therapy information from a plurality of drug delivery apparatuses, wherein the plurality of drug delivery apparatuses comprise at least a first drug delivery apparatus associated with a first subject and a second drug delivery apparatus associated with a second subject, wherein each of the first drug delivery apparatus and the second drug delivery apparatus include a mesh used in the aerosolization of medicament, and wherein the therapy information obtained comprises (i) information related to the breathing patterns of the first subject and the second subject during usage of the first drug delivery apparatus and the second drug delivery apparatus, respectively, and/or (ii) information related to a condition of the mesh included in the first drug delivery device and a condition of the mesh included in the second drug delivery device;

a user interface module configured to generate a definition of a user interface for a user that enables the user to selectively view therapy information obtained by the therapy information acquisition module from the first drug delivery apparatus and the second drug delivery apparatus; and a communications module configured to provide, over a communications network, the definition of the user interface to a client computing platform associated with the user.

2. The system of claim 1, wherein the therapy information acquisition module is configured to obtain the therapy information over the Internet.

3. The system of claim 1, wherein the user interface defined by the definition generated by the user interface module enables the user to input communication directed toward the first user that is based on the therapy information corresponding to the first drug delivery device that is viewed by the user via the user interface, and to input communication directed toward the first user that is based on the therapy information corresponding to the second drug delivery device that is viewed by the user via the user interface, and wherein the communication module is further configured to obtain such communication from the user interface, and to provide the such communication to the appropriate one of the first subject and/or the second subject over a communications network.

4. The system of claim 3, wherein the communication module is configured to provide the communication input by the user to the first subject via one or both of the first drug delivery device and/or a client computing platform associated with the first subject, and to provide communication input by the user to the second subject via one or both of the second drug delivery device and/or a client computing platform associated with the second subject.

5. The system of claim 3, wherein the user interface is defined by the definition generated by the user interface module such that the communications input by the user to the first subject or the subject include communications selected from a predefined set of communications indicating action that the first subject or the second subject should take with respect to mesh of the first drug delivery device or the mesh of the second drug delivery device, respectively.

6. A computer implemented method of enabling one or more users to monitor therapy of a plurality of subjects remotely, wherein such therapy includes the delivery of aerosolized medicament, and wherein the method is implemented by a server comprising one or more processors configured to execute one or more computer program modules, the method comprising:

executing one or more computer program modules on the one or more processors of the server to obtain, over a communications network, therapy information from a plurality of drug delivery apparatuses, wherein the plurality of drug delivery apparatuses comprise at least a first drug delivery apparatus associated with a first subject and a second drug delivery apparatus associated with a second subject, wherein each of the first drug delivery apparatus and the second drug delivery apparatus include a mesh used in the aerosolization of medicament, and wherein the therapy information obtained comprises (i) information related to the breathing patterns of the first subject and the second subject during usage of the first drug delivery apparatus and the second drug delivery apparatus, respectively, and/or (ii) information related to a condition of the mesh included in the first drug delivery device and a condition of the mesh included in the second drug delivery device;

executing one or more computer program modules on the one or more processors of the server to generate a definition of a user interface for a user that enables the user to selectively view therapy information obtained by the therapy information acquisition module from the first drug delivery apparatus and the second drug delivery apparatus; and executing one or more computer program modules on the one or more processors of the server to provide, over a communications network, the definition of the user interface to a client computing platform associated with the user so that the client computing platform presents the user interface to the user.

7. The method of claim 6, wherein the network over which the therapy information is obtained by the server is the Internet.

8. The method of claim 6, wherein the user interface defined by the definition generated by server enables the user to input communication directed toward the first user that is based on the therapy information corresponding to the first drug delivery device that is viewed by the user via the user interface, and to input communication directed toward the first user that is based on the therapy information corresponding to the second drug delivery device that is viewed by the user via the user interface, and wherein the method further comprises:

executing one or more computer program modules on the one or more processors of the server to obtain such communication from the user interface; and executing one or more computer program modules on the one or more processors of the server to provide the such communication to the appropriate one of the first subject and/or the second subject over a communications network.

9. The method of claim 8, wherein the server provides the communication input by the user to the first subject via one or both of the first drug delivery device and/or a client computing platform associated with the first subject, and provides the communication input by the user to the second subject via one or both of the second drug delivery device and/or a client computing platform associated with the second subject.

10. The method of claim 8, wherein the user interface is defined such that the communications input by the user to the first subject or the subject include communications selected from a predefined set of communications indicating action that the first subject or the second subject should take with respect to mesh of the first drug delivery device or the mesh of the second drug delivery device, respectively.

11. A system configured to enable one or more users to monitor therapy of a plurality of subjects remotely, wherein such therapy includes the delivery of aerosolized medicament, the system comprising:

means for obtaining, over a communications network, therapy information from a plurality of drug delivery apparatuses, wherein the plurality of drug delivery apparatuses comprise a first drug delivery apparatus associated with at least a first subject and a second drug delivery apparatus associated with a second subject, wherein each of the first drug delivery apparatus and the second drug delivery apparatus include a mesh used in the aerosolization of medicament, and wherein the therapy information obtained comprises (i) information related to the breathing patterns of the first subject and the second subject during usage of the first drug delivery apparatus and the second drug delivery apparatus, respectively, and/or (ii) information related to a condition of the mesh included in the first drug delivery device and a condition of the mesh included in the second drug delivery device;

means for generating a definition of a user interface for a user that enables the user to selectively view therapy information obtained by the therapy information acquisition module from the first drug delivery apparatus and the second drug delivery apparatus; and means for providing, over a communications network, the definition of the user interface to a client computing platform associated with the user so that the client computing platform presents the user interface to the user.

12. The system of claim 11, wherein the network over which the therapy information is obtained by the means for obtaining is the Internet.

13. The system of claim 11, wherein the user interface defined by the definition generated by the means for generating enables the user to input communication directed toward the first user that is based on the therapy information corresponding to the first drug delivery device that is viewed by the user via the user interface, and to input communication directed toward the first user that is based on the therapy information corresponding to the second drug delivery device that is viewed by the user via the user interface, and wherein the system further comprises:

means for obtaining such communication from the user interface; and means for providing the such communication to the appropriate one of the first subject and/or the second subject over a communications network.

14. The system of claim 13, wherein the means for providing provides the communication input by the user to the first subject via one or both of the first drug delivery device and/or a client computing platform associated with the first subject, and provides the communication input by the user to the second subject via one or both of the second drug delivery device and/or a client computing platform associated with the second subject.

15. The system of claim 13, wherein the user interface is defined such that the communications input by the user to the first subject or the subject include communications selected from a predefined set of communications indicating action that the first subject or the second subject should take with respect to mesh of the first drug delivery device or the mesh of the second drug delivery device, respectively.

* * * * *